US006979468B1

(12) United States Patent
Pollard

(10) Patent No.: US 6,979,468 B1
(45) Date of Patent: Dec. 27, 2005

(54) ORAL COMPOSITION AND METHOD FOR THE TREATMENT OF INFLAMMATORY CUTANEOUS DISORDERS

(75) Inventor: Frank Pollard, Long Grove, IL (US)

(73) Assignee: Sirius Laboratories, Vernon Hills, IL (US)

( * ) Notice: Subject to any disclaimer, the term of this patent is extended or adjusted under 35 U.S.C. 154(b) by 58 days.

(21) Appl. No.: 10/313,165

(22) Filed: Dec. 6, 2002

(51) Int. Cl.$^7$ .................. A61K 31/455; A61K 31/315; A61K 33/30; A61K 33/34; A61P 17/10

(52) U.S. Cl. ...................... 424/643; 424/400; 424/458; 424/468; 424/630; 424/635; 424/637; 424/638; 424/641; 424/643; 514/46; 514/47; 514/249; 514/355; 514/499; 514/859; 514/861; 514/863; 514/864; 514/865; 514/886; 514/887; 514/964

(58) Field of Search ............................ 514/46, 47, 355, 514/859, 861, 863–865, 886–887, 964, 249, 514/499; 424/400, 458, 468, 641, 643, 630, 424/635, 637, 638

(56) References Cited

U.S. PATENT DOCUMENTS

| | | | |
|---|---|---|---|
| 4,505,896 A | 3/1985 | Bernstein | |
| 4,725,609 A | 2/1988 | Kull et al. | |
| 5,459,153 A | 10/1995 | Leung | |
| 5,571,441 A * | 11/1996 | Andon et al. .................. | 252/1 |
| 5,759,559 A | 6/1998 | Fitzjarrell | |
| 5,866,106 A | 2/1999 | Papay | |
| 5,972,382 A | 10/1999 | Majeed et al. | |
| 5,972,985 A | 10/1999 | Thomas et al. | |
| 5,972,999 A | 10/1999 | Murad | |
| 5,989,523 A | 11/1999 | Fitzjarrell | |
| 6,020,351 A | 2/2000 | Pero | |
| 6,133,317 A | 10/2000 | Hart | |
| 6,177,476 B1 * | 1/2001 | Peterson et al. ............. | 514/722 |
| 6,248,763 B1 | 6/2001 | Scivoletto | |
| 6,299,886 B1 | 10/2001 | Piper | |
| 6,361,800 B1 | 3/2002 | Cooper et al. | |
| 6,403,349 B1 | 6/2002 | Mukerji et al. | |
| 6,407,141 B1 | 6/2002 | Hart | |
| 6,660,293 B2 * | 12/2003 | Giordano et al. ............ | 424/439 |
| 2003/0147930 A1 * | 8/2003 | Jun et al. ..................... | 424/401 |

OTHER PUBLICATIONS

Remington's Pharmaceutical Sciences, Mack Publishing Co., Easton (PA), 1985, pp. 1644-1654.*
Kirk-Othmer Encyclopedia of Chemical Technology, 4$^{th}$ rd., John Wiley & Sons, NY, 1993, pp. 274-300.*

* cited by examiner

*Primary Examiner*—John Pak
(74) *Attorney, Agent, or Firm*—Sandra B. Weiss; Jones Day

(57) ABSTRACT

A method and composition for the treatment of acne vulgaris, acne rosacea, and other inflammatory skin conditions comprises the oral administration of a composition comprising a dose of nicotinamide delivered at levels substantially in excess of normal dietary levels, the nicotinamide being delivered in combination with zinc. The composition may also include quantities of copper and folic acid. In a most preferred embodiment, the nicotinamide and copper each are present in immediate release formats, while the zinc is present in a sustained release format.

16 Claims, No Drawings

ORAL COMPOSITION AND METHOD FOR THE TREATMENT OF INFLAMMATORY CUTANEOUS DISORDERS

BACKGROUND OF THE INVENTION

This invention relates to the use of a unique oral preparation for the treatment of inflammatory skin conditions. More particularly, this invention relates to a composition and method for the treatment of inflammatory skin conditions such as acne rosacea and acne vulgaris comprising an immediate release form of nicotinamide in combination with a sustained release form of zinc combined complementary other active ingredients to provide optimum levels of several different treatment modalities. The combination of an immediate release nicotinamide and sustained release zinc provides an unexpected synergistic anti-inflammatory effect that is not observed with combinations of immediate release forms of both chemicals.

Acne vulgaris is an inflammatory disease of the pilosebaceous glands characterized by an eruption of the skin, often pustular in nature but not suppurative. Acne is a common affliction of the adolescent and affects a small but significant percentage of the adult population. Acne lesions are of four basic types: comedones (blackheads or whiteheads), papules, pustules, and cysts (or nodules). Various topical agents are utilized in the treatment of acne and these include sulfur, resorcinol, salicylic acid, benzoyl peroxide, vitamin A acid and topical antibiotics. Other treatment methods include topically applying various scrubbing or abrasive compositions, topically applying deep cleaning or astringent compositions, and also exposure to ultraviolet radiation. Acne involvement can result in unsightly lesions, particularly on the face, and in some cases in severe scarring.

Acne rosacea is another inflammatory skin affliction characterized by erythema with or without an acneiform component (papules, pustules, or nodules). Rosacea typically occurs in adults of about 30–50 years of age. The acneiform component or rosacea has been treated in the past in a fashion similar to the treatment for acne vulgaris. Systemic antibiotics have also been helpful.

Nicotinamide and nicotinic acid are water soluble vitamins whose physiologically active forms include nicotinamide adenine dinucleotide (NAD) and nicotinamide adenine dinucleotide phosphate (NADP). Nicotinamide and nicotinic acid have been used routinely to treat pellagra for which they are therapeutic. Nicotinamide is available from a variety of pharmaceutical houses such as Roche Vitamin, Inc., of Nutley, N.J.; Armor Pharmaceutical Company located in Phoenix Ariz.; Brown Pharmaceutical Company Inc. located in Los Angeles, Calif.; and Keith Pharmaceutical Inc. located in Miami, Fla.

It is known that a high dose of immediate release nicotinamide will have greater bioavailability and greater extended activity than that of a sustained release application.

U.S. Pat. No. 4,505,896 teaches the use of oral compositions containing nicotinamide in the treatment of acne vulgaris. The nicotinamide is administered orally in doses of 100–600 milligrams per day in divided doses taken 2 to 4 times per day. The treatment was reported to decrease inflammatory lesions such as papules, pustules, and cysts, but not comedones.

U.S. Pat. No. 4,725,609 teaches the topical application of nicotinamide to promote angiogenesis, reepithelialization and wound healing.

U.S. Pat. No. 5,459,153 teaches a method for treatment of acne vulgaris comprising administration to a patient of a mixture of pantothenic acid, nicotinic acid, and biotin, to generate nicotinamide in vivo.

U.S. Pat. No. 5,989,523 teaches a topical spray of 1–10% niacinamide with a humectant to treat acne.

U.S. Pat. No. 6,020,351 teaches selectively administering a daily dosage of carotenoids, nicotinamide, and a source of zinc, in excess of normal dietary levels for improving resistance to DNA damage, enhancing DNA repair capacity, and stimulating immune function.

U.S. Pat. No. 6,248,763 teaches the topical application of nicotinamide to treat acne.

It has been reported in the medical literature that acne is often associated with low zinc levels in blood serum and in the epidermal layer. The therapeutic effect of zinc as an anti-inflammatory agent has been well documented, and oral zinc has been reported to be helpful in the treatment of certain types of acne. It is also known that zinc supplementation should be used with copper supplementation to avoid a copper deficiency that might otherwise occur.

SUMMARY OF THE INVENTION

The present invention provides an improved method and composition for the treatment of acne vulgaris, acne rosacea, bullous pemphigoid and other inflammatory skin conditions. The invention relates to the oral administration of a composition comprising a large dose of nicotinamide delivered at levels very substantially in excess of normal dietary levels, the nicotinamide being delivered in immediate release form in combination with a dose of zinc provided in a sustained release form. This combination of immediate release nicotinamide and sustained release zinc provides a level of anti-inflammatory activity substantially exceeding that provided by combinations of immediate release forms of nicotinamide and zinc. The sustained release form of zinc also permits the unopposed absorption of orally administered tetracycline and its cogeners, which are frequently utilized as a part of the treatment regimens for acne vulgaris, acne rosacea and certain other inflammatory cutaneous disorders. In one preferred embodiment of the invention, a quantity of copper is included to avoid the copper deficiency that might otherwise occur due to the zinc supplementation. The composition may also include a quantity of folic acid, which is an essential nutrient in teenagers and women of child-bearing age.

In a most preferred embodiment, nicotinamide and copper and folic acid each are present in immediate release forms, while the zinc is present in a sustained release form. This reduces the interaction between zinc and copper that can reduce the absorption of both. It also reduces the side effects such as nausea that might otherwise be associated with high levels of orally administered zinc

DETAILED DESCRIPTION OF THE INVENTION

The oral composition of the present invention comprises an amount of an immediate release form of nicotinamide very substantially greater than that obtained through the normal diet, combined with a sustained release form of zinc, both delivered in sufficient quantities to provide a therapeutic effect over an extended period for acne vulgaris, acne rosacea, bullous pemphigoid or other inflammatory skin conditions. For purpose of this patent, an immediate release form is one that releases 75% of the active ingredient within two hours of ingestion. A high dose of immediate release nicotinamide increases the bioavailablity of nicotinamide and extends the activity of nicotinamide over that of a sustained release formulation. This unexpected event is unique to oral nicotinamide. The nicotinamide will be present in an amount of at least 250 mg per dose, more preferably at least about 500 mg per dose, and most preferably at least about 750 mg per dose.

In compositions of the present invention, the sustained release form of zinc will be present in an amount sufficient to provide an anti-inflammatory effect. The zinc may be present in any pharmaceutically acceptable zinc salt, zinc complex or zinc chelate for oral administration. Zinc oxide is one such preferred zinc salt. However, other zinc salts such as zinc sulfate and zinc gluconate, zinc complexes or zinc chelates may be substituted, in the sustained release form for the zinc oxide. Zinc oxide can be present in an amount of about at least about 15 mg per dose, more preferably at least about 20 mg per dose, and most preferably at least about 25 mg per doseCompositions within the scope of the present invention may also include a copper-containing compound. Such a copper-containing compound can be any copper compound or copper salt known to be suitable for oral ingestion for copper supplementation, such as cupric oxide or copper salts including cupric sulfate, as well as copper complexes or chelates, but is preferably in an immediate release format. The copper-containing compound should be present in an amount sufficient to compensate for any copper deficiency that might otherwise occur due to the increased levels of zinc. The copper can be present in an amount of about at least 1.0 milligrams per dose, and more preferably in an amount of about at least 1.5 milligrams per dose, regardless of the form of the copper compound used.

The compositions of the present invention may also include a quantity of folic acid. Folic acid is an essential nutrient for a developing fetus. The diets of many teens and young adults are deficient in folic acid. It is expected that the subject invention will be used primarily by teens and young adults who suffer from acne vulgaris. The use of folic acid in compositions of the present invention is intended to supplement this essential nutrient in this segment of the population. The folic acid can be present in the amount of about at least 500 micrograms.

EXAMPLE 1

A composition is prepared in tablet form, each tablet comprising 750 milligrams immediate release nicotinamide, 25 milligrams sustained release zinc oxide, and 500 micrograms immediate release folic acid. When administered orally twice daily, the tablets are found to be a highly effective treatment for acne vulgaris.

EXAMPLE 2

A composition is prepared in tablet form each tablet comprising 750 milligrams immediate release nicotinamide, 25 milligrams sustained release zinc oxide, 500 micrograms immediate release folic acid, and 1.5 milligrams immediate release copper sulfate. When administered orally twice daily, the tablets are found to be a highly effective treatment for acne vulgaris.

EXAMPLE 3

A composition is prepared in tablet form each tablet comprising 1000 milligrams immediate release nicotinamide, 15 milligrams sustained release zinc oxide, 500 micrograms immediate release folic acid, and 1.0 milligrams immediate release copper sulfate. When administered orally twice daily, the tablets are found to be a highly effective treatment for acne vulgaris.

EXAMPLE 4

A composition is prepared in tablet form each tablet comprising 500 milligrams immediate release nicotinamide, 30 milligrams sustained release zinc oxide, 500 micrograms immediate release folic acid, and 1.5 milligrams immediate release copper sulfate. When administered orally twice daily, the tablets are found to be a highly effective treatment for acne vulgaris.

EXAMPLE 5

A composition is prepared in tablet form each tablet comprising 650 milligrams immediate release nicotinamide, 30 milligrams sustained release zinc oxide, 500 micrograms immediate release folic acid, and 1.5 milligrams immediate release copper sulfate. When administered orally twice daily, the tablets are found to be a highly effective treatment for acne vulgaris.

It is to be understood that the invention is not limited to the features and embodiments hereinabove set forth, but may be carried out in other ways without departing from it s spirit.

What is claimed is:

1. An oral pharmaceutical preparation in dosage unit form adapted for administration for the treatment of inflammatory skin disorders, comprising, per dosage unit, at least 250 mg of nicotinamide in an immediate release form, and an amount of zinc in a sustained release form, said amount of zinc being sufficient to provide an enhanced anti-inflammatory effect, in a vehicle pharmaceutically acceptable for oral administration.

2. The oral pharmaceutical preparation of claim 1 wherein said zinc is present as zinc oxide, zinc sulfate, zinc gluconate, zinc complexes or zinc chelates.

3. The oral pharmaceutical preparation of claim 2 wherein said zinc is present as zinc oxide in the amount of about at least 15 mg per dosage unit.

4. The oral pharmaceutical preparation of claim 3 wherein said zinc oxide is present in the amount of about at least 20 mg per dosage unit.

5. The oral pharmaceutical preparation of claim 4 wherein said zinc oxide is present in the amount of about at least 25 mg per dosage unit.

6. The oral pharmaceutical preparation of claim 1 further comprising an amount of folic acid.

7. The oral pharmaceutical preparation of claim 6 wherein said folic acid is present in the amount of at least about 500 micrograms per dosage unit.

8. The oral pharmaceutical preparation of claim 1 wherein said nicotinamide is present in the amount of about at least 500 mg per dosage unit.

9. The oral pharmaceutical preparation of claim 1 wherein said nicotinamide is present in the amount of about at least 750 mg per dosage unit.

10. The oral pharmaceutical preparation of claim 1 further comprising an amount of a copper-containing compound.

11. The oral pharmaceutical preparation of claim 10 wherein said copper-containing compound is in an immediate release form.

12. The oral pharmaceutical preparation of claim 10 wherein said copper-containing compound is selected from the group consisting of cupric oxide, cupric sulfate, copper complexes and copper chelates.

13. The oral pharmaceutical preparation of claim 10 wherein said copper-containing compound is present in an amount of about at least 1.0 milligrams per dosage unit.

14. The oral pharmaceutical preparation of claim 13 wherein said copper-containing compound is present in an amount of about at least 1.5 milligrams per dosage unit.

15. The oral pharmaceutical preparation of claim 1 wherein each dosage unit is in the form of a tablet, capsule or softgel.

16. A method for the treatment of inflammatory skin conditions, the method comprising the step of orally administering to a person having said inflammatory skin condition the oral pharmaceutical preparation of claim 1.

* * * * *

US006979468C1

(12) EX PARTE REEXAMINATION CERTIFICATE (7823rd)
United States Patent
Pollard

(10) Number: US 6,979,468 C1
(45) Certificate Issued: Oct. 19, 2010

(54) ORAL COMPOSITION AND METHOD FOR THE TREATMENT OF INFLAMMATORY CUTANEOUS DISORDERS

(75) Inventor: Frank Pollard, Long Grove, IL (US)

(73) Assignee: Dusa Pharmaceuticals Inc., Wilmington, MA (US)

Reexamination Request:
No. 90/009,562, Aug. 19, 2009

Reexamination Certificate for:
Patent No.: 6,979,468
Issued: Dec. 27, 2005
Appl. No.: 10/313,165
Filed: Dec. 6, 2002

(51) Int. Cl.
*A61K 31/455* (2006.01)
*A61K 31/315* (2006.01)
*A61K 33/30* (2006.01)
*A61K 33/34* (2006.01)
*A61P 17/10* (2006.01)

(52) U.S. Cl. .............. 424/643; 424/400; 424/458; 424/468; 424/630; 424/635; 424/637; 424/638; 424/641; 424/643; 514/46; 514/47; 514/249; 514/355; 514/499; 514/859; 514/861; 514/863; 514/864; 514/865; 514/886; 514/887; 514/964

(58) Field of Classification Search .............. None
See application file for complete search history.

(56) References Cited

U.S. PATENT DOCUMENTS

| | | |
|---|---|---|
| 4,058,557 A | 11/1977 | Douglas et al. |
| 4,115,647 A | 9/1978 | Douglas et al. |
| 4,169,155 A | 9/1979 | Douglas et al. |
| 4,218,450 A | 8/1980 | Douglas et al. |
| 4,242,337 A | 12/1980 | Douglas et al. |
| 4,242,339 A | 12/1980 | Douglas et al. |
| 4,242,340 A | 12/1980 | Douglas et al. |
| 4,440,949 A | 4/1984 | Douglas et al. |
| 4,505,896 A | 3/1985 | Bernstein |
| 4,599,353 A | 7/1986 | Bito |
| 4,661,339 A | 4/1987 | Allen et al. |
| 4,724,230 A | 2/1988 | Cone, Jr. |
| 4,724,234 A | 2/1988 | Cone, Jr. |
| 4,725,609 A | 2/1988 | Kull et al. |
| 4,735,935 A | 4/1988 | McAnalley |
| 4,740,373 A | 4/1988 | Kesselman et al. |
| 4,774,956 A | 10/1988 | Kruse et al. |
| 4,780,451 A | 10/1988 | Donaldson |
| 4,880,628 A | 11/1989 | Allen et al. |
| 4,917,890 A | 4/1990 | McAnalley |
| 4,935,450 A | 6/1990 | Cone, Jr. |
| 4,959,214 A | 9/1990 | McAnalley |
| 4,966,892 A | 10/1990 | McAnalley |
| 5,006,985 A | 4/1991 | Ehret et al. |
| 5,053,396 A | 10/1991 | Blass |
| 5,140,045 A | 8/1992 | Askanazi et al. |
| 5,162,306 A | 11/1992 | Donaldson |
| 5,167,228 A | 12/1992 | Czeisler et al. |
| 5,168,045 A | 12/1992 | Dyer et al. |
| 5,176,133 A | 1/1993 | Czeisler et al. |
| 5,178,882 A | 1/1993 | Kossovsky et al. |
| 5,219,577 A | 6/1993 | Kossovsky et al. |
| 5,251,126 A | 10/1993 | Kahn et al. |
| 5,260,066 A | 11/1993 | Wood et al. |
| 5,288,503 A | 2/1994 | Wood et al. |
| 5,292,538 A | 3/1994 | Paul et al. |
| 5,294,642 A | 3/1994 | Askanazi et al. |
| 5,304,212 A | 4/1994 | Czeisler et al. |
| 5,308,627 A | 5/1994 | Umbdenstock, Jr. |
| 5,334,394 A | 8/1994 | Kossovsky et al. |
| 5,397,803 A | 3/1995 | Smith et al. |
| 5,459,153 A | 10/1995 | Leung |
| 5,460,830 A | 10/1995 | Kossovsky et al. |
| 5,462,750 A | 10/1995 | Kossovsky et al. |
| 5,473,039 A | 12/1995 | Dyer et al. |
| 5,480,865 A | 1/1996 | Kingham |
| 5,494,678 A | 2/1996 | Paradissis et al. |
| 5,518,730 A | 5/1996 | Fuisz |
| 5,571,441 A | 11/1996 | Andon et al. |
| 5,607,975 A | 3/1997 | Smith et al. |
| 5,626,884 A | 5/1997 | Locket |
| 5,642,587 A | 7/1997 | Janes et al. |
| 5,668,134 A | 9/1997 | Klimstra et al. |
| 5,668,155 A | 9/1997 | Cincotta et al. |
| 5,684,045 A | 11/1997 | Smith et al. |
| 5,696,128 A | 12/1997 | Cincotta et al. |
| 5,700,795 A | 12/1997 | Cincotta et al. |
| 5,707,652 A | 1/1998 | Lewy et al. |
| 5,712,265 A | 1/1998 | Cincotta et al. |
| 5,752,235 A | 5/1998 | Kehr et al. |
| 5,759,559 A | 6/1998 | Fitzjarrell |
| 5,763,485 A | 6/1998 | Smith et al. |
| 5,795,861 A | 8/1998 | Kolterman et al. |
| 5,810,737 A | 9/1998 | Dardik |
| 5,830,848 A | 11/1998 | Harrison et al. |
| 5,837,699 A | 11/1998 | Sequeira et al. |
| 5,839,224 A | 11/1998 | Emerson et al. |
| 5,840,331 A | 11/1998 | Van Cauter et al. |
| 5,840,770 A | 11/1998 | Hill |
| 5,866,106 A | 2/1999 | Papay |
| 5,869,084 A | 2/1999 | Paradissis et al. |

(Continued)

FOREIGN PATENT DOCUMENTS

| | | |
|---|---|---|
| WO | WO 01/56572 | 8/2001 |
| WO | WO 01/72286 | 10/2001 |

OTHER PUBLICATIONS

Nisbett, "Evidence–based Zinc Usage", (compiled by Michael John Nisbett, HBScN, RN, MSc (Nutrition) Candidate), updated Apr. 2002.

(Continued)

*Primary Examiner*—Evelyn Huang

(57) ABSTRACT

A method and composition for the treatment of acne vulgaris, acne rosacea, and other inflammatory skin conditions comprises the oral administration of a composition comprising a dose of nicotinamide delivered at levels substantially in excess of normal dietary levels, the nicotinamide being delivered in combination with zinc. The composition may also include quantities of copper and folic acid. In a most preferred embodiment, the nicotinamide and copper each are present in immediate release formats, while the zinc is present in a sustained release format.

U.S. PATENT DOCUMENTS

| Patent No. | | Date | Inventor(s) |
|---|---|---|---|
| 5,949,546 | A | 9/1999 | Lee et al. |
| 5,972,382 | A | 10/1999 | Majeed et al. |
| 5,972,985 | A | 10/1999 | Thomas et al. |
| 5,972,999 | A | 10/1999 | Murad |
| 5,985,281 | A | 11/1999 | Taylorson et al. |
| 5,989,523 | A | 11/1999 | Fitzjarrell |
| 6,020,351 | A | 2/2000 | Pero |
| 6,048,209 | A | 4/2000 | Bailey |
| 6,051,557 | A | 4/2000 | Drucker |
| 6,051,593 | A | 4/2000 | Tang et al. |
| 6,057,307 | A | 5/2000 | Sequeira et al. |
| 6,071,926 | A | 6/2000 | Van Cauter et al. |
| 6,075,020 | A | 6/2000 | Cincotta et al. |
| 6,077,692 | A | 6/2000 | Ruben et al. |
| 6,114,304 | A | 9/2000 | Kolterman et al. |
| 6,114,371 | A | 9/2000 | Tang et al. |
| 6,130,238 | A | 10/2000 | Tang et al. |
| 6,133,317 | A | 10/2000 | Hart |
| 6,136,784 | A | 10/2000 | L'Italien et al. |
| 6,143,717 | A | 11/2000 | Hill |
| 6,177,476 | B1 | 1/2001 | Peterson et al. |
| 6,207,190 | B1 | 3/2001 | Richardson et al. |
| 6,228,388 | B1 | 5/2001 | Paradissis et al. |
| 6,239,105 | B1 | 5/2001 | Brewitt |
| 6,248,763 | B1 | 6/2001 | Scivoletto |
| 6,290,949 | B1 | 9/2001 | French et al. |
| 6,291,505 | B1 | 9/2001 | Huebner et al. |
| 6,293,403 | B1 | 9/2001 | Holmberg |
| 6,299,886 | B1 | 10/2001 | Piper |
| 6,299,896 | B1 | 10/2001 | Cooper et al. |
| 6,313,133 | B1 | 11/2001 | Van Cauter et al. |
| 6,313,158 | B1 | 11/2001 | Tang et al. |
| 6,316,429 | B1 | 11/2001 | Tang et al. |
| 6,316,635 | B1 | 11/2001 | Tang et al. |
| 6,329,375 | B1 | 12/2001 | Tang et al. |
| 6,346,519 | B1 | 2/2002 | Petrus |
| 6,350,754 | B2 | 2/2002 | Tang et al. |
| 6,355,635 | B1 | 3/2002 | Elliott et al. |
| 6,358,508 | B1 | 3/2002 | Ni et al. |
| 6,358,526 | B1 | 3/2002 | Mergens et al. |
| 6,361,800 | B1 | 3/2002 | Cooper et al. |
| 6,365,581 | B1 | 4/2002 | Sequeira et al. |
| 6,387,657 | B1 | 5/2002 | Botstein et al. |
| 6,401,713 | B1 | 6/2002 | Hill et al. |
| 6,403,349 | B1 | 6/2002 | Mukerji et al. |
| 6,406,715 | B1 | 6/2002 | Cefali |
| 6,407,141 | B1 | 6/2002 | Hart |
| 6,417,227 | B1 | 7/2002 | Lord et al. |
| 6,444,218 | B2 | 9/2002 | Han et al. |
| 6,479,545 | B1 | 11/2002 | Levinson et al. |
| 6,482,410 | B1 | 11/2002 | Crossin et al. |
| 6,486,185 | B1 | 11/2002 | McMahon et al. |
| 6,488,956 | B1 | 12/2002 | Paradissis et al. |
| 6,495,129 | B1 | 12/2002 | Li et al. |
| 6,524,619 | B2 | 2/2003 | Pearson et al. |
| 6,559,160 | B1 | 5/2003 | Schall et al. |
| 6,569,868 | B2 | 5/2003 | Tang et al. |
| 6,579,897 | B2 | 6/2003 | Tang et al. |
| 6,583,115 | B1 | 6/2003 | Kopchick et al. |
| 6,604,019 | B2 | 8/2003 | Ahlin et al. |
| 6,605,623 | B1 | 8/2003 | Ko et al. |
| 6,605,699 | B1 | 8/2003 | Ni et al. |
| 6,607,712 | B2 | 8/2003 | Majeed et al. |
| 6,608,029 | B1 | 8/2003 | Kolterman et al. |
| 6,623,768 | B1 | 9/2003 | Naguib |
| 6,623,941 | B1 | 9/2003 | Ruben et al. |
| 6,635,743 | B1 | 10/2003 | Ebner et al. |
| 6,638,950 | B2 | 10/2003 | Duncia et al. |
| 6,638,963 | B1 | 10/2003 | Lewy et al. |
| 6,641,840 | B2 | 11/2003 | Am Ende et al. |
| 6,649,633 | B2 | 11/2003 | Chambers et al. |
| 6,653,323 | B2 | 11/2003 | Moran et al. |
| 6,656,940 | B2 | 12/2003 | Tang et al. |
| 6,660,293 | B2 | 12/2003 | Giordano et al. |
| 6,670,376 | B1 | 12/2003 | Moran et al. |
| 6,673,908 | B1 | 1/2004 | Stanton, Jr. |
| 6,676,967 | B1 | 1/2004 | Cefali et al. |
| 6,677,322 | B2 | 1/2004 | Sequeira et al. |
| 6,677,323 | B2 | 1/2004 | Sequeira et al. |
| 6,683,082 | B2 | 1/2004 | Tang et al. |
| 6,689,607 | B2 | 2/2004 | Ni et al. |
| 6,689,806 | B1 | 2/2004 | Tang et al. |
| 6,693,077 | B1 | 2/2004 | Ruben et al. |
| 6,696,066 | B2 | 2/2004 | Kaiko et al. |
| 6,696,083 | B1 | 2/2004 | Paradissis et al. |
| 6,696,448 | B2 | 2/2004 | Tang et al. |
| 6,696,463 | B2 | 2/2004 | Tang et al. |
| 6,699,873 | B1 | 3/2004 | Maguire et al. |
| 6,723,713 | B2 | 4/2004 | Sequeira et al. |
| 6,740,338 | B1 | 5/2004 | Chopra |
| 6,740,655 | B2 | 5/2004 | Magee et al. |
| 6,743,448 | B2 | 6/2004 | Kryger |
| 6,743,613 | B2 | 6/2004 | Ni et al. |
| 6,746,691 | B2 | 6/2004 | Cefali |
| 6,753,164 | B2 | 6/2004 | Ni et al. |
| 6,756,208 | B2 | 6/2004 | Griffin et al. |
| 6,756,401 | B2 | 6/2004 | Day et al. |
| 6,759,411 | B2 | 7/2004 | Ko et al. |
| 6,770,466 | B2 | 8/2004 | Shi et al. |
| 6,777,194 | B1 | 8/2004 | Gerdes et al. |
| 6,780,857 | B2 | 8/2004 | Ko et al. |
| 6,787,336 | B1 | 9/2004 | Kopchick et al. |
| 6,794,379 | B2 | 9/2004 | Medina et al. |
| 6,797,698 | B1 | 9/2004 | Van Den Berghe |
| 6,811,773 | B1 | 11/2004 | Gentz et al. |
| 6,818,229 | B1 | 11/2004 | Cefali et al. |
| 6,824,993 | B2 | 11/2004 | Soppet et al. |
| 6,828,327 | B2 | 12/2004 | Kuo et al. |
| 6,828,333 | B2 | 12/2004 | Marfat et al. |
| 6,835,547 | B1 | 12/2004 | Gosling et al. |
| 6,835,866 | B1 | 12/2004 | Mangelsdorf et al. |
| 6,849,413 | B2 | 2/2005 | Young et al. |
| 6,849,641 | B1 | 2/2005 | Tang et al. |
| 6,869,945 | B2 | 3/2005 | Marfat et al. |
| 6,875,776 | B2 | 4/2005 | Ko et al. |
| 6,894,041 | B2 | 5/2005 | Marfat et al. |
| 6,897,234 | B2 | 5/2005 | Ko et al. |
| 6,900,016 | B1 | 5/2005 | Venter et al. |
| 6,906,066 | B2 | 6/2005 | Ko et al. |
| 6,919,368 | B2 | 7/2005 | Ko et al. |
| 6,947,790 | B2 | 9/2005 | Gevins et al. |
| 6,953,790 | B2 | 10/2005 | Burgey et al. |
| 6,962,718 | B2 | 11/2005 | Ramaeckers |
| 6,974,836 | B2 | 12/2005 | Carter et al. |
| 6,974,869 | B2 | 12/2005 | Delucca |
| 6,984,651 | B2 | 1/2006 | Duncia et al. |
| 6,992,084 | B2 | 1/2006 | Schall et al. |
| 6,998,239 | B1 | 2/2006 | Gosling et al. |
| 2002/0044961 | A1 | 4/2002 | Kirschner et al. |
| 2002/0061870 | A1 | 5/2002 | Pearson et al. |
| 2003/0147930 | A1 | 8/2003 | Jun et al. |
| 2004/0101554 | A1 | 5/2004 | Kirschner et al. |
| 2005/0037065 | A1 | 2/2005 | Kirschner et al. |

OTHER PUBLICATIONS

Remington's Pharmaceutical Sciences, Mack Publishing Co., Easton (PA), 1985, pp. 1644–1654.

Kirk–Othmer Encyclopedia of Chemical Technology, 4th rd., John Wiley & Sons, NY, 1993, pp. 274–300.

Goransson, K. et al., Oral Zinc in Acne Vulgaris: A Clinical and Methodological Study, Acta Dermavenereol (Stockhlom), 58(5):443–448 (1978) (Abstract).

Hillstrom, L, et al., Comparison of Oral Treatment with Zinc Sulphate and Placebo in Acne Bulgaris, British Journal of Dermatology, 97(6):681–684 (1977) (Abstract).

Briggs, M., Acne Vulgaris–Zinc Deficiency?. Med. J. Aust., Jun. 26, 1976, pp. 1019, vol. 15 No. 26.

Fitzherbert, J.C., Letter: Acne Vulgaris–Zinc Deficiency?, Med. J. Aust, May 29, 1976, pp. 848.

Fitzherbert, J.C., Acne Vulgaris–Zinc Deficiency?, Med. J. Aust., Aug. 14, 1976, pp. 273, Bolume 2, No. 7.

Frommer, D.J., The Healing of Gastric Ulcers By Zinc Sulphate, Med. J. Aust., Nov. 22, 1976, pp. 793–796, vol. 2, No. 21.

Zhu, Xiaodong, et al., Changes of Trace Elements in Serum of Patients with Acne Vulgaris (English Language Abstract), Guandong Science Trace Elements (Chinese), 2002, vol. 8.

Advertisement for Nicomide by Sirius Laboratories, Inc.

Webster GF, "Managing the Inflammatory Response in Acne," Journal of the American Academy of Dermatology: 33:247–253 (1995).

Ma, Alice and Medenica, Maria, "Response_of Generalized Granuloma Annulare to High–Dose Niacinamide," Arch Dermatol, vol. 119:836–839 (1983).

Berk, Mark Allan and Lorinez, Allan L., "The Treatment of Bullous Pemphigold With Tetracycline and Niacinamide," Arch Dermatol, vol. 122:670–674 (Jun. 1986).

Kolhler, Irmgard K. and Lorinez, Allan L., "Erythema Elevaturn Diutinum Treated With Niacinamide and Tetracycline," Arch Dermatol, vol. 116: 693–695 (Jun. 1980).

Fivenson, et al., "Nicotinamide and Tetracycline Therapy of Bullous Pemphigoid," Arch Dermatol, vol. 130:753–758 (Jun. 1994).

Handfield–Jones, S., et al., "High Dose Nicotinamide in the Treatment of Necrobiosis Lipoldica," British Journal of Dermatology, vol. 118:693–696 (1988).

Bernstein, Joel E., "Nicotinamide and Sulfapyridine," Winston Laboratories, Inc., Ch. 11:235–241 (undated).

Michaelsson, G. and Ljunghall, K, "Patients with Dermatitis Herpetiformis, Acne, Psoriasis and Darier's Disease Have Low Epidermal Zinc Concentrations," Acta Derm Venereol (Stockh), vol. 70:304–308 (1990).

Michaelsson, Gerd, "Oral Zinc in Acne," Acta Dermatovener (Stockholm), Suppl. 89:87–93 (1980).

Amer, et al., "Serum Zinc in Acne Vulgaris," International Journal of Dermatology, vol. 21:481–484 (Oct. 1982).

Petley, et al., "The Pharmacokinetics of Nicotinamide in Humans and Rodents,"Diabetes, vol. 44:152–155 (Feb. 1995).

Sandstead, Harold H., "Requirements and Toxicity of Essential Trace Elements, Illustrated by Zinc and Copper," Am J Clin Nutr, vol. 61 (Suppl.):621S–624S (1995).

Fischer, Peter, et al., "The Effect of Dietary Zinc on Intestinal Copper Absorption,", The American Journal of Clinical Nutrition, vol. 34:1670–1675 (Sep. 1981).

O'Dell, Boyd L., "Mineral Interactions Relevant to Nutrient Requirements," Symposium: Nutrients in Infant Formulas, pp. 1832–1838 (Undated).

Mapp, R.K., et al., "The Effect of Zinc Sulphate and of Bicitropeptide on Tetracycline Absorption", SA Medical Journal, Supplement—South African Journal of Laboratory and Clinical Medicine, 50, Oct. 23, 1976, pp. 1829–1830.

Lomaestro, Ben M., et al., "Absorption Interactions With Fluoroquinolones", Drug Safety 12(5), Adis International Limited, 1995, pp. 314–333.

Penttila O., et al., "Effect of Zinc Sulphate on the Absorption of Tetracycline and Coxycycline in Man", Europ. J.Clinical Pharmacol, 9., Springer–Verlag, 1975, pp. 131–134.

Shakeri–Nejad, Kasra, et al., "Drug Interactions During Therapy With Three Major Groups of Antimicrobial Agents", Expert Opinion, Pharmacother, 7(6), 2006, pp. 639–651.

Nicomide Training Manual, Chapter 4, Cambridge Publications, Inc., Undated, (Brookline, MA), pp. 1–34.

Verma, K.C. et al., Oral Zinc Sulphate Therapy in Acne Vulgaris: A Double Blind Trial, Act Dermavenerol (Stockholm), 60:337–340 (1980) (Abstract).

US 6,979,468 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-16 are cancelled.

New claims 17-24 are added and determined to be patentable.

*17. An oral dosage form for the treatment of inflammatory skin disorders consisting essentially of 750 milligrams of nicotinamide in immediate release form, 25 milligrams of zinc oxide in sustained release form, 1.5 milligrams of cupric oxide in immediate release form, and 500 micrograms of folic acid in immediate release form.*

*18. A method of treating a patient suffering from an inflammatory skin disorder comprising the step of administering to said patient an oral dosage form, wherein said an oral dosage form consists essentially of 750 milligrams of nicotinamide in immediate release form, 25 milligrams of zinc oxide in sustained release form, 1.5 milligrams of cupric oxide in immediate release form, and 500 micrograms of folic acid in immediate release form.*

*19. The oral dosage form of claim 17, wherein said oral dosage form is a tablet.*

*20. The oral dosage form of claim 17, wherein said oral dosage form is a capsule.*

*21. The oral dosage form of claim 17, wherein said oral dosage form is a softgel.*

*22. The method of claim 18, wherein said oral dosage form is a tablet.*

*23. The method of claim 18, wherein said oral dosage form is capsule.*

*24. The method of claim 18, wherein said oral dosage form is a softgel.*

* * * * *